United States Patent [19]

Haslanger

[11] 4,192,891
[45] Mar. 11, 1980

[54] PROSTACYCLIN ANALOGS AND THEIR USE IN INHIBITION OF ARACHIDONIC ACID-INDUCED PLATELET AGGREGATION AND BRONCHOCONSTRICTION

[75] Inventor: Martin F. Haslanger, Lambertville, N.J.

[73] Assignee: E. R. Squibb & Sons, Inc., Princeton, N.J.

[21] Appl. No.: 33,368

[22] Filed: Apr. 25, 1979

[51] Int. Cl.$^2$ .................... C07C 177/00; C07C 69/38; C07C 69/74
[52] U.S. Cl. ................................... 424/305; 424/317; 560/119; 562/501; 260/448.8 R
[58] Field of Search ...................... 560/119; 562/501; 424/305, 317

[56] References Cited
PUBLICATIONS

Nicolaov et al., Chem. Comm. 1067 (1978).

*Primary Examiner*—Robert Gerstl
*Attorney, Agent, or Firm*—Lawrence S. Levinson; Burton Rodney

[57] ABSTRACT

Prostacyclin analogs are provided having the structure

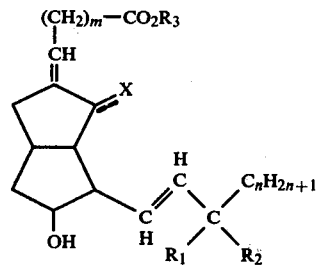

wherein $=\!\!\!=\!\!\!X$ represents $=\!\!\!\!O$ or OH, $R_1$ and $R_2$ are OH or H, provided at least one of $R_1$ and $R_2$ is other than hydroxyl, $R_3$ is H or alkyl of 1 to 4 carbons, m is an integer of from 2 to 5, and n is an integer of from 2 to 10, or pharmaceutically acceptable salts thereof. These compounds have been found to be potent inhibitors of arachidonic acid-induced platelet aggregation and bronchoconstriction.

22 Claims, No Drawings

PROSTACYCLIN ANALOGS AND THEIR USE IN INHIBITION OF ARACHIDONIC ACID-INDUCED PLATELET AGGREGATION AND BRONCHOCONSTRICTION

BACKGROUND OF THE INVENTION

Prostacyclin, an organic compound related to prostaglandins, is (5Z)-9-deoxy-6,9α-epoxy-Δ$^5$-PGF$_{1α}$ and is represented by the formula

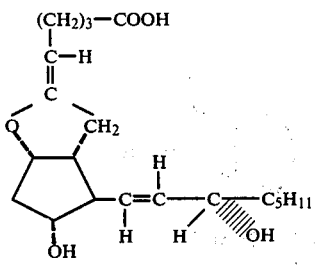

For its synthesis and structure see for example R. A. Johnson et al., J. Am. Chem. Soc. 99, 4182 (1977) and Prostaglandins 12, 915 (1976), and E. J. Corey et al, cited, J. Am. Chem. Soc. 99, 20006 (1977). For some of its biological properties and uses see the references cited in the Johnson references. Prostacyclin is referred to as "PGI$_2$", see Anonymous, Prostaglandins 13, 375 (1977).

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin synthetase inhibitors.

Because of these biological responses, prostacyclin and prostacyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent postoperative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes.

Prostacyclin and prostacyclin-type compounds are extremely potent in causing stimulation of smooth muscle, and are also highly active in potentiating other known smooth muscle stimulators, for example, oxytocic agents; they are also useful in reducing the undesirable gastrointestinal effects resulting from systemic administration of anti-inflammatory prostaglandin synthetase inhibitors. In addition, prostacyclin or prostacyclin-type compounds are useful in the treatment of asthma. For example, these compounds are useful as bronchodilators or as inhibitors of mediators, such as SRS-A and histamine which are released from cells activated by an antigen-antibody complex.

Prostacyclin or prostacyclin-type compounds are also useful in treating peripheral vascular disease in humans. The term peripheral vascular disease as used herein means disease of any of the blood vessels outside of the heart and to disease of the lymph vessels.

A complete description of the various uses of prostacyclin or prostacyclin-type compounds is set out in U.S. Pat. No. 4,124,599.

DESCRIPTION OF THE INVENTION

In accordance with the present invention, there is provided new prostacyclin analogs having the structure

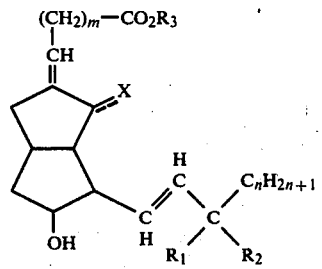

wherein=X represents =O or OH, R$_1$ and R$_2$ are OH or H, provided that at least one of R$_1$ and R$_2$ is other than hydroxyl, R$_3$ is hydrogen or lower alkyl containing 1 to 4 carbons, m is an integer of from 2 to 5, and n is an integer of from 2 to 10, or pharmaceutically acceptable salts thereof. The above compounds are effective in inhibiting arachidonic acid-induced platelet aggregation and bronchoconstriction.

Thus, the compounds of the invention may be represented by the following

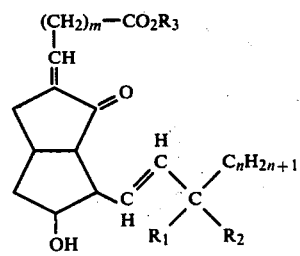

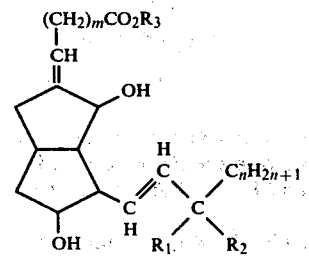

Preferred are isomers of the following structure

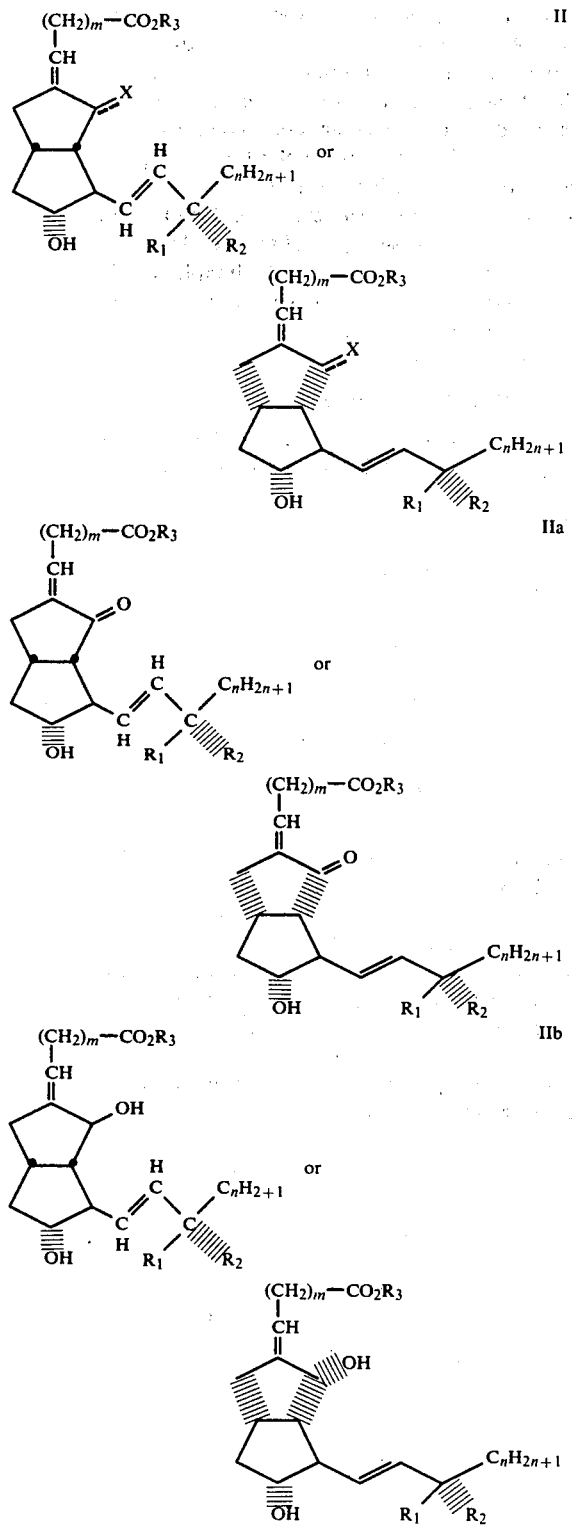

In the above compounds of the invention, it is preferred that m is 3 or 4 and n is 4, 5, or 6, $R_3$ is hydrogen and one of $R_1$ and $R_2$ is hydroxyl and the other hydrogen.

The compounds of formula I may be prepared according to the following procedure.

Bicyclo[3.3.0]oct-7-en-2-one

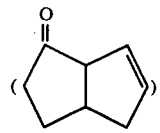

(cf. Crandall et al., J. Org. Chem., 32, 532 (1967)) is reacted with a halogenating agent such as N-bromoacetamide or N-bromosuccinimide, in a solution containing water at room temperature to form a halohydrin

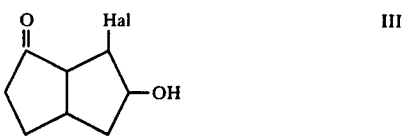

wherein Hal is Cl, Br or I.

The hydroxyl hydrogen of compounds, such as III may be replaced by a blocking group such as tetrahydropyranyl, t-butyldimethylsilyl, or ethoxy ethyl by the appropriate methods (cf. Grieco, et al., J. Org. Chem. 42, 3772 (1977), Corey et al., J. Am. Chem. Soc., 94, 6190 (1972)) to give a protected halohydrin of the formula

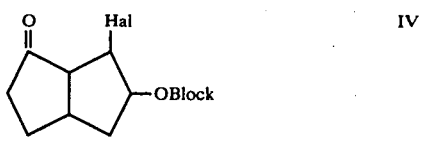

The halo-ketone IV is then dehydrohalogenated by treatment with a base, such as 1,5-diazabicyclo[5.4.0]undecene or 1,5-diazabicyclo[4.3.0]nonene (cf. Fieser, Vol. 1, p. 1308, Wiley, N.Y. 1967), in an aprotic solvent such as toluene or benzene, to give an $\alpha,\beta$ unsaturated ketone

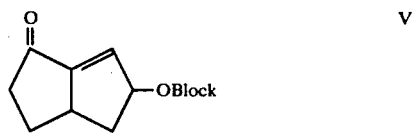

The product of formula V is then allowed to undergo a 1,4 conjugate addition to the $\alpha,\beta$ unsaturated ketone functionality with a cuprate reagent, such as

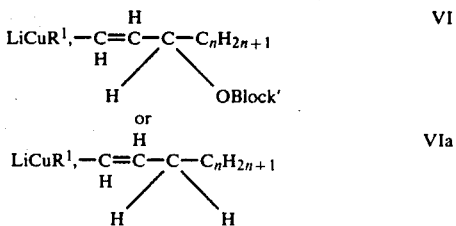

(in the case where both $R_1$ and $R_2$ are hydrogen) (where $R^1$ is any suitable ligand, Block' is a protecting group, cf. Posner, Org. React., 19, 1 (1972), S. L. Chen et al., J. Org. Chem. 43, 3450 (1978), E. J. Corey et al., J. Org.

Chem. 43, 3418 (1978)) in a solvent such as ether or THF at −80° to −20° to yield

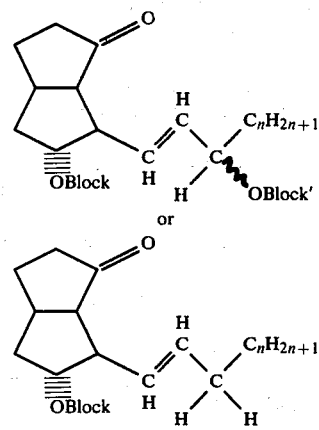

VII

VIIa (in the case where R$_1$ and R$_2$ are each hydrogen).

If Block' is such that it is hydrolyzed in the workup of the 1,4 conjugate addition, another protecting group for the allylic hydroxyl may be put on at this stage under the appropriate conditions (see above).

The ketone formula VII or VIIa is then treated with a strong base, for example, lithium diisopropyl amide or lithium tetramethyl piperdide, in a solvent such as ether or THF, at −80° to 0°, followed by an aldehyde such as

VIII and the subsequent aldol product (cf Heathcock et al, J. Am. Chem. Soc., 99, 248 (1977)) is dehydrated to give an enone

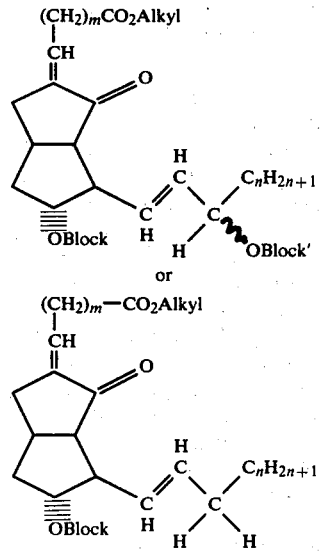

IX

IXa

The blocking groups on the hydroxyl function may be removed at this point by treatment with the appropriate reagents (see references cited above) to give the compound

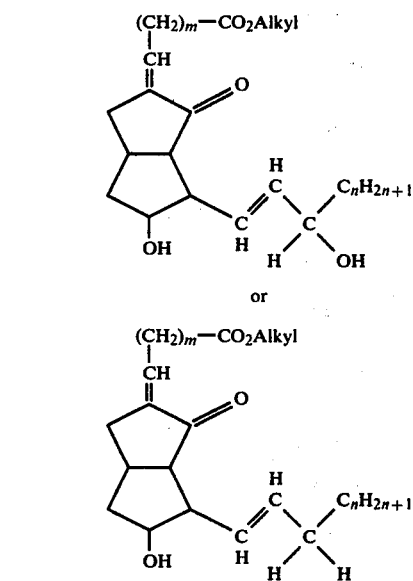

X

Xa

The isomers at the allylic alcohol center may be separated at this point by chromatography on silica gel. The carboxylate ester may be hydrolyzed by treatment with a basic aqueous medium such as LiOH, NaOH or KOH in aqueous THF followed by neutralization to the free acid of formula

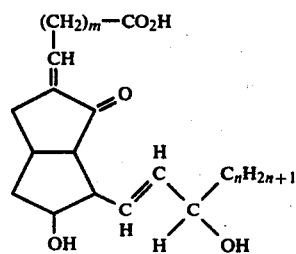

XI

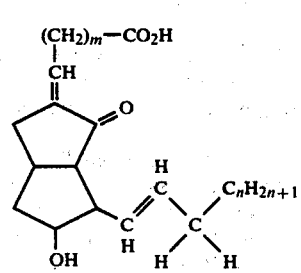

XIa

The enones of formula X or Xa may be reduced with sodium borohydride, lithium diisobutyl aluminum hydride, or zinc borohydride to the compound of formula XII or XIIa

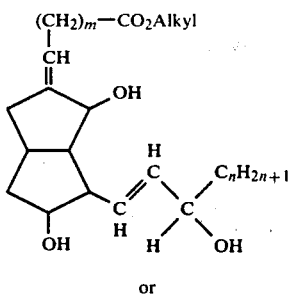

XII or

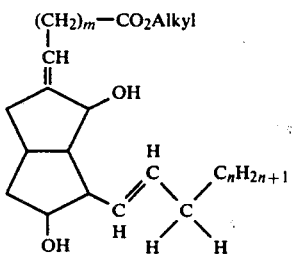

XIIa

In a manner like that used for the hydrolysis of compound X or Xa, the formula XII or XIIa compound may be converted to the formula XIII or XIIIa compound of the invention.

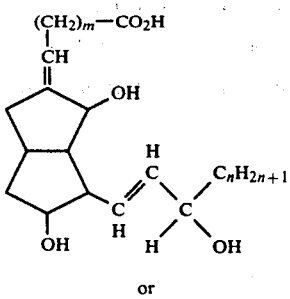

XIII or

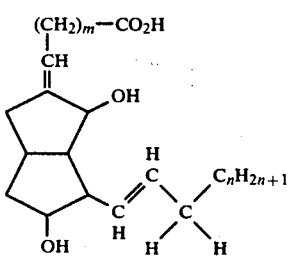

XIIIa

The compounds of this invention can exist in various stereoisomeric forms as well as optical isomers. These various forms including mixtures thereof are within the scope of the invention.

The aldehyde esters such as formula VIII may be prepared by a variety of methods, see for example, Noller and Adams, J. Am. Chem. Soc., 48, 1074 (1926).

The inhibition of platelet aggregation according to the present invention is obtained by contacting blood platelets with a concentration of from about 1 to about 1600 μM of the prostacyclin analogs of formula I.

The compounds of formula I may be employed in the free form or in the form of their base addition salts.

Compounds of formula I may form physiologically acceptable base addition salts with alkali metal or alkaline earth metal bases, such as sodium hydroxide, potassium hydroxide or calcium hydroxide. These salts frequently provide useful means for isolating the products from reaction mixtures by forming the salt in a medium in which it is insoluble. The free base may then be obtained by neutralization, e.g., with an acid.

The compounds of formula I including their pharmaceutically acceptable salts have exhibited the ability to inhibit arachidonic acid induced platelet aggregation and bronchoconstriction according to the general procedures described by Nijkamp et al, supra, Born, G. V. R., "Aggregation of Blood Platelets by Adenosine Diphosphate and Its Reversal," Nature 194:927–929, 1962 and Amdur and Mead, "Mechanics of Respiration in Unanesthetized Guinea Pigs," Amer. J. Physiol., 192, 364–368 (1958) as modified by Giles et al, "The Bronchodilator and Cardiac Stimulant Effects of Th 1165a, Salbutamol, and Isoproterenol," J. Pharmacol. Exp. Ther. 186, 472–481 (1973). Thus, the compounds of formula I may be useful in the treatment or prevention of myocardial ischemia, angina pectoris, myocardial infarction, stroke and transcient ischemic attacks, diabetes, intravascular inflammation, asthma, anaphylactic shock, atherosclerosis, endotoxin shock, certain viral conditions and systemic and pulmonary hypertension.

The compounds of formula I including their pharmaceutically acceptable salts can be administered orally or parenterally to various mammalian species in amounts ranging from about 1 to about 100 mg/kg/day divided into one or more doses for the pharmaceutical purpose set forth above. The compounds are formulated with an inert carrier according to conventional pharmaceutical practice, for example in the form of tablets, capsules, or an injectable solution.

The following Examples represent preferred embodiments of the invention.

EXAMPLE 1

[3aS-[2(E),3aα,5β,6α(E,R),6aα]]-5-[Hexahydro-5-hydroxy-6-(3-hydroxy-1-octenyl)-1-oxo-2(1H)-pentalenylidene]pentanoic acid, methyl ester A. (3aα,5α)-tetrahydro-5-hydroxy-1(2H)-pentalenone, t-butyldimethylsilyl ether To an ice cooled solution of 2.1 g (17.5 mmol) of bicyclo[3.3.0]oct-7-en-2-one in 80% aqueous acetone (50 ml) is added 2.62 g (19 mmol) of N-bromoacetamide in one portion. The reaction mixture is allowed to warm to ambient temperature and stir for 14 hours. The reaction mixture is then concentrated in vacuo, diluted with ether and the ether solution is washed with saturated KHCO₃ and brine. After drying, the solvent is removed to yield 2.93 g of bromohydrin. To an ice cooled solution of the bromohydrin (13.5 mmol) and 2.24 g (14.8 mmol) of t-butyldimethylsilyl chloride in DMF (15 ml) is added 2.01 g of imidazole. The reaction mixture is allowed to warm to ambient temperature and stir for 16 hours. The reaction mixture is poured into ether and water, the ether phase is washed with water, pH 5.5 buffer, saturated KHCO₃, brine and dried (MgSO₄). The solvent is evaporated to yield 4 g of crude silyl ether. To a solution of the silyl ether in benzene (20 ml) is added 1,5-diazabicyclo[5.4.0]undecene (DBU) (1.8 g). The resulting solution is stirred at ambient temperature for 4 hours then poured into ether and water. The ether phase is washed with pH 5.5 buffer, saturated KHCO₃, brine and dried (MgSO₄). The solvent is evaporated to yield 3 g of crude product which is chromatographed on silica to yield 1.78 g of the title enone (42% yield from starting ketone). $^{13}$C nmr: (ppm relative to TMS, CDCl$_3$), 203.3, 147.3, 136.3, 82.3, 46.8, 46.2, 42.2, 29.9, 25.8, 18.0, −4.8.

B.
[3aS[3aα,5β,6α(E,R)6aα]]-5-hexahydro-5-t-butyldimethylsilyloxy-6-(3-t-butyldimethylsilyloxy-1-octenyl)-1(2H)pentalenone To a −78° solution of the mixed cuprate from lithium 3-methoxy-3-methylbutyne, CuBr.SMe$_2$, and 3-(t-butyldimethylsilyloxy)octenyl lithium in ether-THF (10:1) is added a solution of 1.5 g (6 mmol) of the silyl ether of 7-hydroxybicyclo[3.3.0]oct-1,8-en-2-one in ether. After 5 minutes at −78° the reaction is quenched with HOAc (12 mmol) in ether. The crude reaction mixture is poured into ether and washed with saturated NH$_4$Cl, saturated KHCO$_3$ and brine. After drying the solvent is evaporated to yield the crude product which is chromatographed on silica to yield 1.3 g (45%) of [3aS[3aα,5β,6α(E,R)6aα]]-5-hexahydro-5-t-butyldimethylsilyloxy-6-(3-t-butyldimethylsilyloxy-1-octenyl)-1(2H)pentalenone as an oil.

C.
[3aS-[2(E),3aα,5β,6α(E,R),6aα]]-5-[hexahydro-5-t-butyldimethylsilyloxy-6-(3-t-butyldimethylsilyloxy-1-octenyl)-1-oxo-2(1H)-pentalenylidene]pentanoic acid, methyl ester To a solution of lithium diisopropylamide (2 mmol) in ether (4 ml) at −78° is added the octenyl-bicyclo [3.3.0] octanone (2 mmol) in ether (6 ml). The resulting solution is stirred at −78° for 10 minutes then 5-methoxycarbonylpentanal (2.6 mmol) is added rapidly. After 4 minutes at −78° the reaction is quenched with HOAc in ether. The reaction mixture is poured into ether and saturated NH$_4$Cl. The ether phase is washed with brine and dried (MgSO$_4$). The solvent is evaporated to yield 1.2 g of crude ketol product. To a solution of the crude β-hydroxy ketone in benzene (10 ml) and methanesulfonyl chloride (2.2 mmol) is added triethylamine (2.2 mmol) in benzene (2 ml). The resulting reaction mixture is stirred at ambient temperature for ½ hour then 0.3 ml of 1,5-diazabicyclo[5.4.0]undecene in benzene (1 ml) is added. The resulting mixture is stirred at ambient temperature for 1 hour then poured into pH 5.5 buffer and ether. The ether phase is washed with saturated KHCO$_3$, brine and dried (MgSO$_4$). The solvent is evaporated to yield the crude enone which is chromatographed on silica to yield 280 mg of enone (24% yield). $^{13}$C nmr: (ppm relative to TMS, CDCl$_3$), 207.6, 173.6, 138.7, 134.5, 134.2, 129.7, 76.7, 73.4, 56.7, 56.0, 51.4, 42.6, 38.3, 33.5, 33.3, 31.8, 28.9, 25.9, 25.6, 24.9, 23.6, 22.6, 18.2, 17.8, 14.0, −4.2, −4.7, −5.0.

D.
[3aS-[2(E),3aα,5β,6α(E,R)6aα]]-5-[hexahydro-5-hydroxy-6-(3-hydroxy-1-octenyl)-1-oxo-2(1H)-pentalenylidene]pentanoic acid, methyl ester A solution of the bis-silyl ether (174 mg) and pyridinium tosylate (100 mg) in methanol is heated at 55°–60° for 22 hours. The cooled mixture is poured into ether and half-saturated brine. The ether phase is washed with brine and dried (MgSO$_4$). The solvent is evaporated to yield 85 mg of crude diol which is chromatographed on silica to yield 22 mg of the title compound. $^{13}$C nmr: (ppm relative to TMS, CDCl$_3$), 207.9, 173.6, 138.0, 136.2, 134.9, 130.8, 78.4, 72.4, 56.5, 55.1, 51.5, 41.5, 37.1, 33.5, 32.5, 31.7, 28.9, 25.1, 23.5, 22.6, 14.0.

EXAMPLE 2

[3aS-[2(E),3aα,5β,6α(E,R),6aα]]-5-[Hexahydro-5-hydroxy-6-(3-hydroxy-1-octenyl)-1-oxo-2(1H)-pentalenylidene]pentanoic acid To a solution of the ester enone (19 mg) of Example 1 in 80% aqueous THF at 0° is added 0.5 ml of 1 N LiOH solution. The resulting solution is stirred for 4 hours at ∼5° then acidified to pH 3 with saturated oxalic acid solution. The reaction mixture is poured into ether and brine. The brine is reextracted (2×) with ether. The combined ether extracts are dried (Na$_2$SO$_4$) and the solvent is evaporated to yield 18 mg of the title compound. $^{13}$C nmr: (ppm relative to TMS, CD$_3$CN), 207.9, 174.9, 139.5, 136.0, 135.3, 132.0, 79.3, 72.8, 57.5, 55.8, 42.5, 38.4, 34.7, 33.7, 32.9, 32.6, 29.5, 25.9, 24.4, 23.4, 14.3.

EXAMPLE 3

[3aS-[2(E),3aα,5β,6α(E,S*),6aα]]-5-[Hexahydro-5-hydroxy-6-(3-hydroxy-1-octenyl)-1-oxo-2(1H)-pentalenylidene]pentanoic acid, methyl ester

A.
(3aα,5α,6β,6aα)-6-Bromohexahydro-5-hydroxy-1(2H)-pentalenone, 2-tetrahydropyranyl ether To an ice cold solution of 4.7 g (0.039 mole) of bicyclo[3.3.0]oct-7-ene-2-one in 80% aqueous acetone (120 ml) is added 8.04 g (0.058 mole) of N-bromoacetamide in one portion. The reaction mixture is allowed to warm to ambient temperature and stirred for 14 hours. The reaction mixture is then concentrated in vacuo, diluted with ether and the ether solution is washed with saturated solution of NaHSO$_3$, KHCO$_3$ and brine. After drying the solvent is removed to yield 6.8 g of crude bromohydrin. The compound is purified by recrystallization from ether and pentane. $^{13}$C NMR (ppm relative to TMS, CDCl$_3$) 218.4, 80.4, 60.8, 57.2, 39.0, 37.2, 36.9, 26.7.

A solution of 6.8 g (31 mmol) of bromohydrin, 3.9 g (46 mmol) of dihydropyran and 50 mg of pyridinium tosylate in CH$_2$Cl$_2$ (150 ml) is stirred at ambient temperature for 4 hours. The reaction mixture is then diluted with ether, washed with half saturated NaCl, then washed with saturated NaCl and dried (MgSO$_4$). The solvent is evaporated to yield 7.9 g of the protected bromohydrin.

B. (3aα,5α)-Tetrahydro-5-hydroxy-1(2H)-pentalenone, 2-tetrahydropyranyl ether To an ice cooled solution of 7.9 g (26 mmol) of the bromo ketone in benzene (100 ml) is added dropwise 11.9 g (80 mmol) of DBU. The reaction is stirred and warmed to ambient temperature over 3 hours. The reaction mixture is then poured into ether and water, the layers are separated and the ether phase is washed with pH 5.5 acetate buffer, saturated KHCO$_3$, saturated NaCl and dried (MgSO$_4$). The solvent is evaporated to yield 5.2 g of the enone.

C.
[3aα,5β,6α(E),6aα]-5-Hexahydro-5-tetrahydropyranyloxy-6-(3-hydroxy-1-octenyl)-1(2H)-pentalenone To a solution of 16 mmol of the mixed cuprate from lithium 3-methoxy-3-methylbutyne, CuBr.SMe$_2$ and 3-(methoxyisopropyloxy)-octenyl lithium in ether-THF (10:1) at −78° is added a solution of the enone (8 mmol) in ether. After 10 minutes at −78° the reaction is quenched with HOAc (16 mmol) in ether. The reaction mixture is diluted with ether, washed with saturated NH$_4$Cl, 1 N HCl, saturated KHCO$_3$, saturated NaCl and dried (MgSO$_4$). The solvent is evaporated to yield the crude product which is chromatographed on silica (hexane-ethyl acetate) to yield 0.8 g of the conjugate addition product.

D.
[3aα,5β,6α(E),6aα]-5-Hexahydro-5-hydroxy-6-(3-hydroxy-1-octenyl)-1(2H)-pentalenone, bis 2-tetrahydropyranyl ether A solution of 1.32 g (4 mmol) of the allylic alcohol, 0.5 g (6 mmol) of dihydropyran and 50 mg of pyridinium tosylate in CH$_2$Cl$_2$ is stirred at ambient temperature for 4 hours. The reaction mixture is diluted with ether, washed with half saturated NaCl, saturated NaCl and dried (MgSO$_4$). The solvent is evaporated to yield 1.4 g of the protected ketone.

E.
[2(E),3aα,5β,6α(E,S),6aα]-5-[Hexahydro-5-hydroxy-6-(3-hydroxy-1-octenyl)-1-oxo-2(1H)pentalenylidene]-pentanoic acid, methyl ester To a solution of 2.1 mmol of lithium diisopropyl amide in ether (2 ml) at −78° is added a solution of the octenyl-bicyclo[3.3.0]octanone (2 mmol) in ether (8 ml). The resulting solution is stirred at −78° for 10 minutes then 5-methoxycarbonylpentanal (3 mmol) is added rapidly (neat). After 5 minutes the reaction is quenched with HOAc (2.1 mmol) in Et$_2$O at −78°. The reaction mixture is allowed to warm to ambient temperature and then diluted with ether. The ether solution is washed with pH 5.5 acetate buffer, saturated KHCO$_3$, saturated NaCl and dried (MgSO$_4$). The solvent is evaporated to yield 1.1 g of crude ketol.

To an ice cooled solution of the crude ketol in benzene (8 ml) is added 240 mg (2.1 mmol) of mesyl chloride followed by a solution of 222 mg (2.2 mmol) of Et$_3$N in benzene (1 ml). The reaction mixture is allowed to warm to ambient temperature and stirred for ½ hour. A solution of DBU in benzene (1 ml) is added dropwise and the resulting solution is stirred at ambient temperature for 1 hour. The reaction mixture is then poured into ether and pH 5.5 acetate buffer. The ether phase is washed with saturated KHCO$_3$, saturated NaCl and dried (MgSO$_4$). The solvent is evaporated to yield 1 g of crude enone.

A solution of crude enone in 10 ml of methanol containing 50 mg of pyridinium tosylate is heated at 55°–60° for 3 hours. The methanol is evaporated to yield a thick oil which is triturated with ether to precipitate the pyridinium tosylate. The crude enone is chromatographed on silica with ethyl acetate-hexane (4:1) to yield 82 mg of the 15β isomer (R$_f$=0.24)±[3aS-[2(E),3aα,5β,6α(E,R),6aα]]-5-[hexahydro-5-hydroxy-6-(3-hydroxy-1-octenyl)-1-oxo-2(1H)-pentalenylidene]pentanoic acid, methyl ester and 80 mg of the 15α isomer (R$_f$=0.21)±-[3aS[2(E),3aα,5β,6α(E,S),6aα]]-5-[hexahydro-5-hydroxy-6-(3-hydroxy-1-octenyl)-1-oxo-2(1H)-pentalenylidene]pentanoic acid, methyl ester $^{13}$C nmr: (ppm relative to TMS, CDCl$_3$), 207.8, 173.6, 138.0, 136.3, 134.9, 131.3, 78.4, 72.7, 56.4, 55.2, 51.5, 41.4, 37.3, 33.4, 32.4, 31.7, 29.0, 25.1, 23.6, 22.6, 14.0.

EXAMPLE 4
[3aS-[2(E),3aα,5β,6α(E,S*),6aα]]-5-[Hexahydro-5-hydroxy-6-(3-hydroxy-1-octenyl)-1-oxo-2(1H)-pentalenylidene]pentanoic acid To an ice cooled solution of 75 mg (0.2 mmol) of the 15α-ester of Example 3 in 80% aqueous THF (10 mg) is added 1.5 ml of 1 N LiOH. The resulting solution is stirred with continued cooling for 1.75 hour, then acidified to pH 3 with saturated oxalic acid solution. The reaction mixture is poured into ether and saturated NaCl and the layers are separated. The aqueous phase is reextracted (twice) with ether and the combined ether extracts are dried (MgSO$_4$). The solvent is evaporated to yield 47 mg of the title compound. $^{13}$C nmr: (ppm relative to TMS, CD$_3$CN). 208.7, 175.0, 139.5, 136.1, 135.3, 132.0, 79.3, 72.9, 57.4, 55.8, 42.5, 38.3, 34.7, 33.7, 32.9, 32.6, 29.5, 25.9, 24.4, 23.4, 14.3.

EXAMPLE 5
[3aS-[2(E),3aα,5β,6α(E,R),6aα]]-5-[Hexahydro-5-hydroxy-6-(3-hydroxy-1-octenyl)-1-hydroxy-2(1H)-pentalenylidene]pentanoic acid, methyl ester To a solution of 190 mg (0.5 mmol) of [3aS-[2(E),3aα,5β,6α(E,R),6aα]]-5-[hexahydro-5-hydroxy-6-(3-hydroxy-1-octenyl)-1-oxo-2(1H)-pentalenylidene]pentanoic acid, methyl ester and 200 mg of cerium chloride heptahydrate in methanol (5 ml) chilled to 0° is added portionwise 40 mg of sodium borohydride. The reaction mixture is stirred at room temperature for 5 to 10 minutes, then treated with saturated ammonium chloride solution and extracted with ethyl acetate. The combined ethyl acetate extracts are washed with saturated NaCl, dried (MgSO$_4$) and concentrated in vacuo to yield 180 mg of [3aS-[2(E),3aα,5β,6α-(E,R),6aα]]-5-[hexahydro-5-hydroxy-6-(3-hydroxy-1-octenyl)-1-hydroxy-2(1H)pentalenylidene]pentanoic acid, methyl ester.

EXAMPLE 6
[3aS-[2(E),3aα,5β,6α(E,R),6aα]]-5-[Hexahydro-5-hydroxy-6-(3-hydroxy-1-octenyl)-1-hydroxy-2(1H)-pentalenylidene]pentanoic acid To an ice cooled solution of 75 mg (0.2 mmol) of the above ester in 80% aqueous THF (10 mg) is added 1.5 ml of 1 N LiOH. The resulting solution is stirred with continued cooling for 1.75 hour, then acidified to pH 3 with saturated oxalic acid. The reaction mixture is poured into ether and saturated NaCl and the layers are separated. The aqueous phase is reextracted (twice) with ether and the combined ether extracts are dried (MgSO$_4$). The solvent is evaporated to yield the title compound.

EXAMPLE 7

Following the procedure of Example 5, except substituting as the starting material the product of Example 3, the corresponding hydroxyl derivative of the methyl ester, namely, [3aS-[2(E),3aα,5β,6α(E,S),6aα]]-5-[hexahydro-5-hydroxy-6-(3-hydroxy-1-octenyl)-1-hydroxy- 2(1H)-pentalenylidene]pentanoic acid, methyl ester is obtained.

EXAMPLE 8

Following the procedure of Example 6, except substituting as the starting material the product of Example 7, the corresponding hydroxyl derivative of the acid, namely, [3aS-[2(E),3aα,5β,6α(E,S),6aα]]-5-[hexahydro-5-hydroxy-6-(3-hydroxy-1-octenyl)-1-hydroxy-2(1H)-pentalenylidene]pentanoic acid is obtained.

EXAMPLE 9

[3aS-[2(E),3aα,5β,6α(E),6aα]]-5-[Hexahydro-5-hydroxy-6-(1-octenyl)-1-oxo-2(1H)-pentalenylidene]-pentanoic acid, methyl ester Following the procedure of Example 1 except employing 1-octenyl lithium in place of 3-(t-butyldimethylsilyloxy)octenyl lithium in the mixed cuprate, the title compound is obtained.

the corresponding hydroxyl derivative of the methyl ester, namely, [3aS-[2(E),3aα,5β,6α(E),6aα]]-5-[hexahydro-5-hydroxy-6-(1-octenyl)-1-hydroxy-2(1H)-pentalenylidene]pentanoic acid, methyl ester is obtained.

EXAMPLE 12

Following the procedure of Example 6, except substituting as the starting material the product of Example 11, the corresponding hydroxyl derivative of the acid, namely, [3aS-[2(E),3aα,5β,6α(E),6aα]]-5-[hexahydro-5-hydroxy-6-(1-octenyl)-1-hydroxy-2(1H)-pentalenylidene]pentanoic acid, is obtained.

EXAMPLES 13 TO 18

Following the procedure of Example 1 except substituting for 3-(t-butyldimethylsilyloxy)-octenyl lithium in the cuprate complex, the compound shown in Column I of Table A below, and substituting for 5-methoxycarbonyl pentanal, the compound shown in Column II, the product shown in Column III is obtained.

TABLE A

| Ex. No. | n | m | R₃ | n | m | R₃ |
|---|---|---|---|---|---|---|
| 13. | 2 | 2 | CH₃ | | | |
| 14. | 4 | 3 | C₂H₅ | as in Column I | as in Column II | |
| 15. | 7 | 4 | C₃H₇ | | | |
| 16. | 8 | 5 | C₄H₉ | | | |
| 17. | 5 | 2 | C₂H₅ | | | |
| 18. | 10 | 3 | CH₃ | | | |

EXAMPLE 10

[3aS-[2(E),3aα,5β,6α(E),6aα]]-5-[Hexahydro-5-hydroxy-6-(1-octenyl)-1-oxo-2(1H)-pentalenylidene]-pentanoic acid Following the procedure of Example 2, except employing the product of Example 9 as the starting material, the title compound is obtained.

EXAMPLE 11

Following the procedure of Example 5, except substituting as the starting material the product of Example 9,

EXAMPLES 19 TO 24

Following the procedure of Example 2 except substituting for 3-(methoxyisopropyloxy)octenyl lithium, the compound shown in Column I of Table B below, and substituting for 5-methoxycarbonylpentanal, the compound shown in Column II, the compound shown in Column III is obtained.

TABLE B

| Ex. No. | n | m | R₃ | n | m | R₃ |
|---|---|---|---|---|---|---|
| 19. | 2 | 2 | CH₃ | as in Column I | as in Column II | |

TABLE B-continued

| | Column I | Column II | Column III |
|---|---|---|---|
| | Li-CH=CH-CH(C$_n$H$_{2n+1}$)-O-C(CH$_3$)(OCH$_3$)(CH$_3$) | HC(=O)-(CH$_2$)$_m$-CO-R$_3$ | (bicyclic structure with (CH$_2$)$_m$-CO$_2$R$_3$, C$_n$H$_{2n+1}$, OH, OH) |
| Ex. No. | n | m | R$_3$ |
| 20. | 4 | 3 | C$_2$H$_5$ |
| 21. | 7 | 4 | C$_3$H$_7$ |
| 22. | 8 | 5 | C$_4$H$_9$ |
| 23. | 5 | 2 | C$_2$H$_5$ |
| 24. | 10 | 3 | CH$_3$ |

EXAMPLES 25 TO 36

Following the procedure of Example 5, except substituting as the starting material, the ester products of Examples 13 to 24, the corresponding hydroxyl derivatives are obtained.

EXAMPLES 37 TO 48

Following the procedure of Example 2 or 4, except substituting as the starting material, the ester products of Examples 13 to 24, the corresponding acid derivatives are obtained.

EXAMPLES 49 TO 60

Following the procedure of Example 5, except substituting as the starting material, the acid derivatives of Examples 37 to 48, the corresponding hydroxy derivatives are obtained,

EXAMPLES 61 TO 66

Following the procedure of Example 9, except employing as the lithium compound in the cuprate complex, the compound shown in Column I of Table C below, and substituting for the 5-methoxycarbonyl pentanal, the compound shown in Column II, the product shown in Column III is obtained.

EXAMPLES 67 TO 72

Following the procedure of Example 5, except substituting as the starting material, the ester products of Examples 61 to 66, the corresponding hydroxyl derivatives are obtained.

EXAMPLES 73 TO 78

Following the procedure of Example 2 or 4, except substituting as the starting material, the ester products of Examples 61 to 66, the corresponding acid derivatives are obtained.

EXAMPLES 79 TO 84

Following the procedure of Example 5, except substituting as the starting material, the acid derivatives of Examples 73 to 78 the corresponding hydroxy derivatives are obtained.

EXAMPLES 85 AND 86

Inhibition of Arachidonic Acid Induced Platelet Aggregation

Venous blood is collected from the antecubital vein of human volunteers who are drug free for at least one week. The blood is collected by gravity into plastic transfer bags containing 0.38% sodium citrate as the anticoagulant. Platelet-rich plasma (PRP) is prepared by centrifuging the citrated blood at 200× g for 10

TABLE C

| | Column I | | | Column II | | | Column III | | |
|---|---|---|---|---|---|---|---|---|---|
| | Li-CH=CH-CH$_2$-C$_n$H$_{2n+1}$ | | | HC(=O)-(CH$_2$)$_m$-CO-R$_3$ | | | (bicyclic structure with (CH$_2$)$_m$-CO$_2$R$_3$, C$_n$H$_{2n+1}$, OH, H, H) | | |
| Ex. No. | n | | | m | R$_3$ | | n | m | R$_3$ |
| 61. | 2 | | | 2 | CH$_3$ | | | | |
| 62. | 4 | | | 3 | C$_2$H$_5$ | | as in Column I | as in Column II | |
| 63. | 7 | | | 4 | C$_3$H$_7$ | | | | |
| 64. | 8 | | | 5 | C$_4$H$_9$ | | | | |
| 65. | 5 | | | 2 | C$_2$H$_5$ | | | | |
| 66. | 10 | | | 3 | CH$_3$ | | | | | minutes at 25° C. Platelet-poor plasma (PPP) is obtained by centrifuging the PRP at 2500× g for 30 minutes at 25° C.

Platelet aggregation is studied photometrically (Born, Nature 194:927–929, 1962) using a Chronolog Aggregometer connected to a linear recorder. Each of the test compounds ([3aS-[2(E),3aα,5β,6α(E),6aα]]-5-[hexahydro-5-hydroxy-6-(3-hydroxy-1-octenyl)-1-oxo-2(1H)-pentalenylidene]pentanoic acid (Example 2) and [3aS-[2(E),3aα,5β,6α(E,S*),6aα]]-5-[hexahydro-5-hydroxy-6-(3-hydroxy-1-octenyl)-1-oxo-2(1H)-pentalenylidene]pentanoic acid (Example 4)) is dissolved in methanol and preincubated with PRP for 2.5 minutes at 37° C. Arachidonic acid (400 μM) dissolved in 0.1 M Tris-HCl buffer, pH 8.5, is then added and the optical transmission recorded for at least 3 minutes. The rate of increase in optical transmission, which is a measure of the initial velocity of aggregation, is measured for each text mixture by determining the slope of the steepest part of the curve.

The test compounds are found to be 100% effective in inhibiting platelet aggregation at the screening concentration of 1 mM. and have $I_{50}$ (concentration to achieve 50% inhibition) values of 50–500 μM.

What is claimed is:

1. A compound of the structure

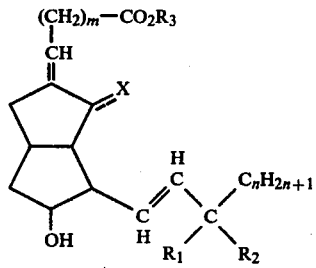

wherein =X represents =O or —OH, $R_1$ and $R_2$ are OH or H, provided at least one of $R_1$ and $R_2$ is other than hydroxyl, $R_3$ is hydrogen or lower alkyl containing 1 to 4 carbons, m is an integer of from 2 to 5, and n is an integer of from 2 to 10, and pharmaceutically acceptable salts thereof, and isomers thereof.

2. The compound as defined in claim 1 wherein =X is =O.

3. The compound as defined in claim 1 wherein =X is —OH.

4. The compound as defined in claim 1 wherein m is 3 and n is 5.

5. The compound as defined in claim 1 wherein $R_1$ is OH and $R_2$ is H.

6. The compound as defined in claim 1 wherein $R_1$ and $R_2$ are each hydrogen.

7. The compound as defined in claim 1 wherein $R_3$ is alkyl.

8. The compound as defined in claim 1 wherein $R_3$ is H.

9. The compound as defined in claim 1 wherein $R_3$ is alkyl, and X is =O.

10. The compound as defined in claim 1 wherein $R_3$ is alkyl, and X is OH.

11. The compound as defined in claim 1 wheren $R_3$ is H, and X is =O.

12. The compound as defined in claim 1 wherein $R_3$ is H, and X is OH.

13. The compound a defined in claim 1 having the structure

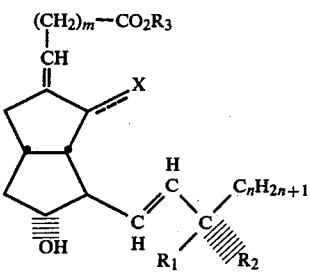

14. The compound as defined in claim 13 having the structure

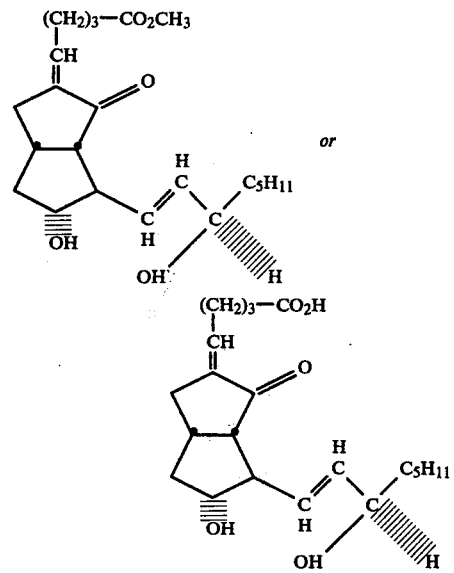

15. The compound as defined in claim 13 having the structure

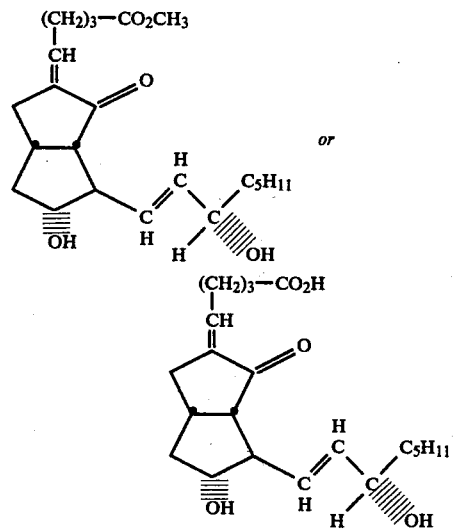

16. The compound as defined in claim 13 having the structure

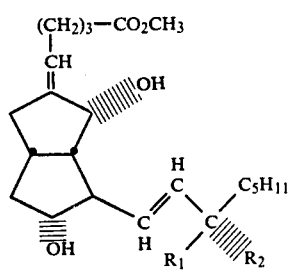

or

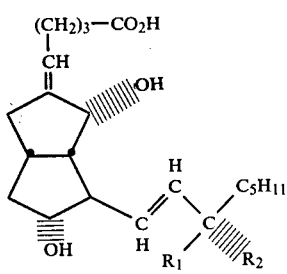

17. The compound as defined in claim 1 having the structure

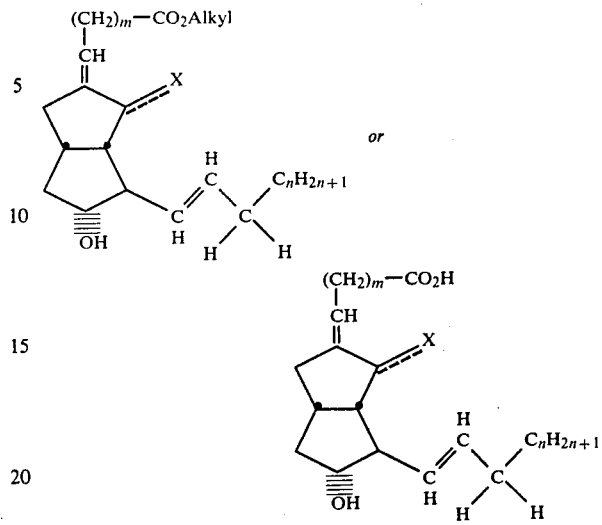

18. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

19. The method as defined in claim 18 wherein said compound is administered in an amount within the range of from about 1 to about 100 mg/kg.

20. A composition for inhibiting arachidonic acid-induced platelet aggregation and bronchoconstriction, comprising a compound as defined i claim 1 or a pharmaceutically acceptable salt thereof, and a parmaceutically acceptable carrier therefor.

21. A method of inhibiting platelet aggregation which comprises administering to a mammalian host an effective amount of a compound as defined in claim 1 or a pharmaceutically acceptable salt thereof.

22. A method of inhibiting bronchoconstriction associated with asthma, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,192,891
DATED : March 11, 1980
INVENTOR(S) : Martin F. Haslanger

It is certified that error appears in the above-identified patent and that said Letters Patent are hereby corrected as shown below:

Column 2, next to the first structure insert --I--.
Column 2, next to the second structure insert --Ia--.
Column 2, next to the third structure insert --Ib--.
Column 3, line 47, structure IIb, the portion "-$C_nH_{2+1}$" should read -- -$C_nH_{2n+1}$ --.
Column 17, line 19, "text" should read --test--.
Column 18, line 1, "a" should read --as--.
Column 20, line 35, "i" should read --in--.

Signed and Sealed this

Twenty-second Day of July 1980

[SEAL]

Attest:

SIDNEY A. DIAMOND

Attesting Officer     Commissioner of Patents and Trademarks